United States Patent [19]

Yamaguchi et al.

[11] Patent Number: 5,048,601

[45] Date of Patent: Sep. 17, 1991

[54] SHELL-AND-TUBE APPARATUS HAVING AN INTERMEDIATE TUBE PLATE

[75] Inventors: Katsunobu Yamaguchi; Tateo Kurihara, both of Yokohama; Isamu Yanai; Kazuo Kikuchi, both of Yokosuka; Tomoo Saito; Suguru Hamanaka, both of Yokohama; Teruo Nagai, Chigasaki; Yasuyuki Sakakura, Yokkaichi; Takeshi Shibano, Yokkaichi; Yoji Kawatani, Yokkaichi; Tadahiko Kondoh, Yokkaichi, all of Japan

[73] Assignees: JGC Corporation; Mitsubishi Petrochemical Co., Ltd., both of Tokyo, Japan

[21] Appl. No.: 481,023

[22] Filed: Feb. 16, 1990

[30] Foreign Application Priority Data

Feb. 17, 1989 [JP] Japan .................................. 1-37542
Feb. 17, 1989 [JP] Japan .................................. 1-37543

[51] Int. Cl.⁵ .............................................. F28D 7/10
[52] U.S. Cl. ..................................... 165/140; 165/83; 165/158; 422/201
[58] Field of Search .................... 165/82, 83, 140, 158; 422/201, 197

[56] References Cited

U.S. PATENT DOCUMENTS

| | | | |
|---|---|---|---|
| 2,986,454 | 5/1961 | Jewett | 165/140 |
| 3,001,766 | 9/1961 | Laist | 165/140 X |
| 3,982,585 | 9/1976 | Gribsvad | 165/83 |
| 4,157,114 | 6/1979 | De Lorenzo | 165/158 |
| 4,256,783 | 3/1981 | Takada et al. | 422/197 |

FOREIGN PATENT DOCUMENTS 916172 8/1954 Fed. Rep. of Germany ...... 165/140

Primary Examiner—Allen J. Flanigan
Attorney, Agent, or Firm—Armstrong, Nikaido, Marmelstein, Kubovcik, & Murray

[57] ABSTRACT

A shell-and-tube apparatus, more specifically, a shell-and-tube reactor, which includes a vessel, at least one intermediate tube plate sectioning the interior of the vessel into at least two compartments having different temperatures, a number of heat transferring tubes penetrating the intermediate tube plate or plates, and a fluid passing through the tubes which is heated or cooled by a heat transfer medium surrounding the tubes. At least one insulation plate or plates are provided on one or both sides of the intermediate tube plate so that the space between the intermediate tube plate or plates and, if two or more insulation plates are used, the space or spaces between the insulation plates may be utilized as a stagnation zone for the heat transfer medium, so as to make the temperature gradient through the intermediate tube plate or plates gentle and relax the thermal stress occurring in the body wall. The reactor is particularly useful for production of (meth)acrolain and/or (meth)acrylic acid by catalytic gas-phase oxidation of propylene or butenes.

5 Claims, 6 Drawing Sheets

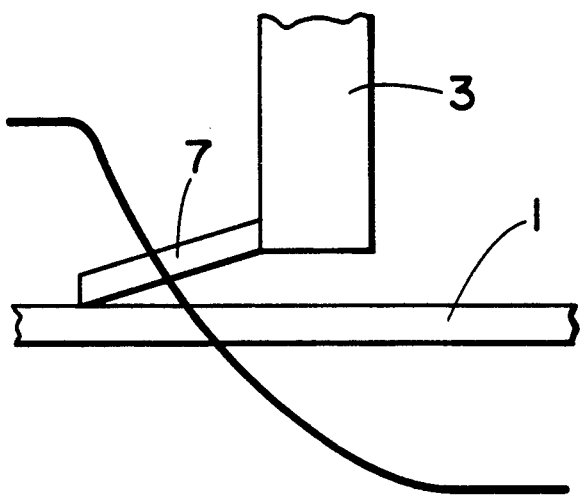
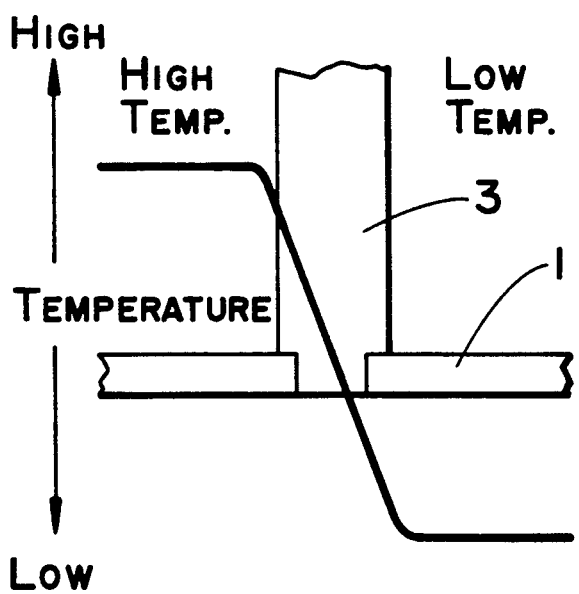
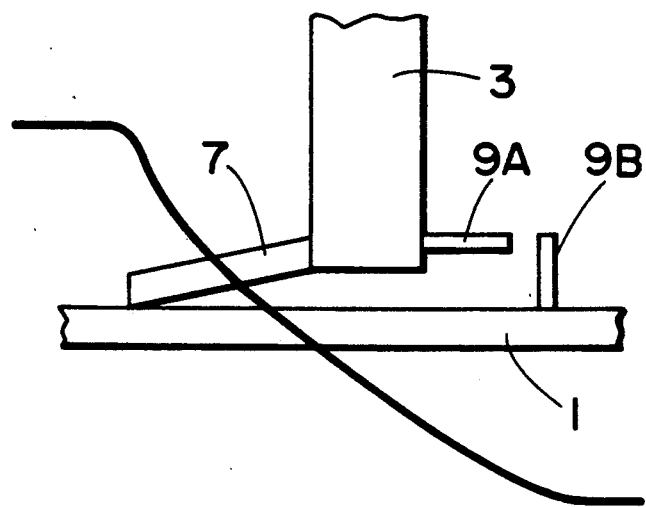

SHELL-AND-TUBE APPARATUS HAVING AN INTERMEDIATE TUBE PLATE

BACKGROUND OF THE INVENTION

1. Field of the Invention

The present invention concerns an improved shell-and-tube apparatus having an intemediate tube plate, specifically, a shell-and-tube reactor. The invention is particularly useful when applied to the apparatus for producing (meth)acrylic acid by catalytic gas-phase oxidation of propylene or butenes.

2. State of the Art

There are many processes in which quenching of reaction gas is neccessary, for example, the process for producing acrylic acid by catalytic gas-phase oxidation of propylene. As the reaction apparatus for practicing such a process, a shell-and-tube reactor having an intermediate tube plate is the most suitable.

The shell-and-tube reactor having an intemediate tube plate is a reactor of the structure having, in addition to an intermediate tube plate which sections the reactor into two compartments, a high temperature compartment and a low temperature compartment, plural reaction tubes penetrating the tube plate, thereby to heat or cool the reactant substances passing through the reaction tubes with a heat transfer medium surrounding the tubes.

In reference to the above mentioned process for producing acrylic acid from propylene, the material propylene gas is introduced with air and an inert gas (nitrogen or steam) into the reaction tubes in the high temperature side (reaction zone), and is converted to acrolain and acrylic acid by a solid catalyst packed in the reaction tubes.

After completion of the reaction, the gas is immediately cooled in the same reaction tube at the low temperature side (quenching zone) without being transferred to another vessel for the purpose of preventing undesirable side reactions. In an alternative embodiment, two kinds of catalysts are packed in a series in each reaction tube, and propylene is converted partly into acrolain and partly into acrylic acid by the first catalyst, and then, the acrolain is further converted to acrylic acid by the second catalyst so that the yield of the acrylic acid may increase. In the latter embodiment, it is necessary to carry out the respective reactions at the most suitable temperatures, and therefore, the reaction gas is rapidly cooled or heated at different positions of the same reacion tubes.

In order to quench the reaction gas in the former process, it is essential to keep the temperature difference between the reaction zone and the quenching zone of the reaction vessel. This causes heat transfer from the reaction zone by way of the intermediate tube plate to the quenching zone, and makes it sometimes difficult to keep the quenching zone at a determined temperature. The large temperature difference causes large thermal stress in the intermediate tube plate and the body wall to which the intermediate tube plate is fitted. The same problem resides more or less in regard to the rapid heating and quenching in the latter process.

The simplest way of fitting up the intermediate tube plate to the reaction vessel is, as shown in FIG. 5A and FIG. 5B, to weld the intermediate tube plate 2 as it is to the body wall 1.

In this case of direct welding the intermediate tube plate to the body wall, however, if the temperature difference between the two compartments of both sides of the plate is very large, the temperature gradient at the body wall near the intermediate tube plate is so steep that strong thermal stress occurs in the body wall. If the temperature difference rises above a certain level, the thermal stress exceeds the allowable stress of the body wall and the vessel may be destroyed. This is a particularly serious problem for vessels having thick intermediate tube plates.

Therefore, the reaction vessels are often constructed into two separate parts of different temperatures, i.e., the compartment of the reaction zone and the compartment of the quenching zone, and then, to connect the parts at the flanges thereof using a gasket therebetween; in other words, to form a shell and tube reaction vessel having two intermediate tube plates.

In this type of the reaction vessel there is an improvement that the thermal stress in the tube plates is not so large due to the lack of the intermediate tube plate at which a significant temperature difference is posed. However, there is a space between the reaction zone and the quenching zone, and therefore, the rate of cooling cannot exceed a certain limit. Also, the cost of manufacturing the apparatus becomes higher because the two tube plates are used.

SUMMARY OF THE INVENTION

The object of the present invention is to provide shell-and-tube apparatus, specifically, shell-and-tube reactors in which transfer of heat from the high temperature compartment to the low temperature compartment is surpressed to a minimum and rapid cooling or heating is maintained, the temperature difference between the both sides of the intermediate tube plate is kept small and the thermal stress in the body wall is decreased, and thus, an increase of the manufacturing cost can be avoided.

BRIEF EXPLANATION OF THE DRAWINGS

FIG. 5A showing the whole, and FIG. 5B showing the enlarged part in the circle of FIG. 5A.

FIG. 9, FIG. 10 and FIG. 11 are conceptional graphs like FIG. 3 and FIG. 4, showing the temperature gradient at the joint part of the body wall and the intermediate tube plate.

DETAILED EXPLANATION OF THE PREFERRED EMBODIMENTS

Figure 1:
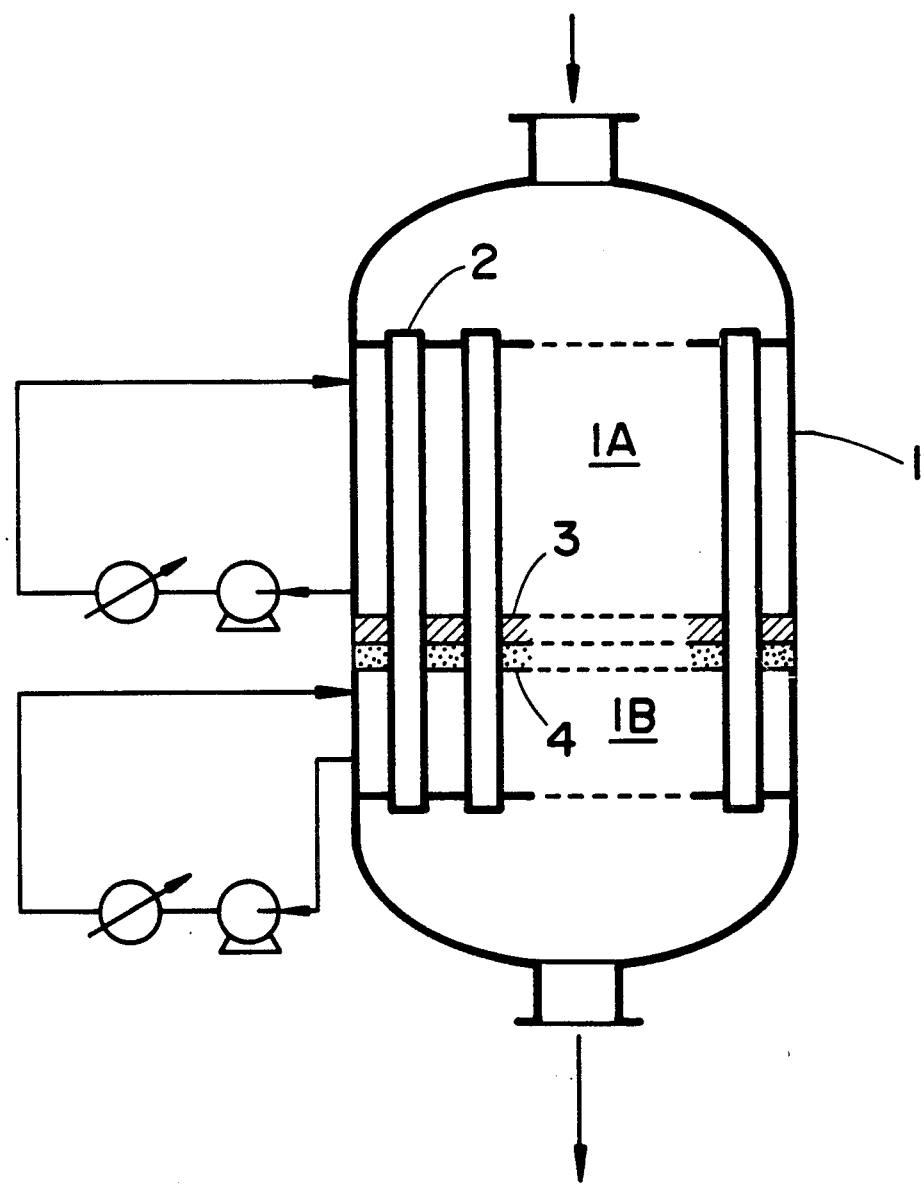
FIG. 1 is a sectional view of the shell and tube apparatus according to the present invention with reference to a shell-and-tube reaction vessel which is a typical example.

The shell-and-tube apparatus of the present invention is, as shown in FIG. 1 with reference to a shell-and-tube reactor which is a typical example, an apparatus comprising a vessel 1, at least one intermediate tube plate 3 for sectioning the vessel into two compartments of different temperatures, the high temperature compartment 1A and the low temperature compartment 1B in the shown example, and plural heat transfer tubes 2 are fitted in apertures to penetrate the plate and taking the role of the reaction tubes, and being of the type in which the fluid passing through the tubes is heated or cooled by the heat transfer medium surrounding the tubes, characterized in that at least one insulation plate 4 is provided at one or both sides of the intermediate tube plate 3 to form a zone or layer of liquid 6, where little movement of the heat transfer medium takes place, i.e., a stagnation zone between the intermediate tube plate 3 and the insulation plate 4, and, if two or more insulation plates are used, also between the insulation plates.

Figure 2:
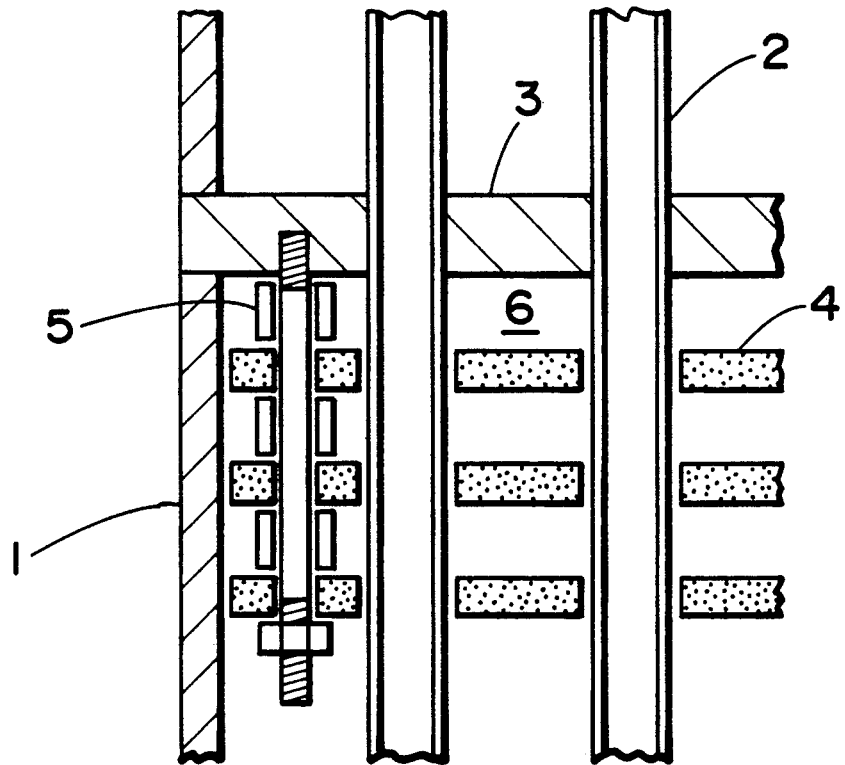
FIG. 2 is an enlarged sectional view of an intermediate tube plate showing a preferred embodiment of configuration of the thermal insulation plates.

The embodiment shown in FIG. 2 uses spacers 5 to ensure the formation of the above explained stagnation zone.

The insulation plates can be made of metal plates, but it is preferable to use materials of a low thermal conductivity such as ceramics, particularly, thick plates thereof so that the resistance to heat transfer may be larger. Anyway, it is necessary to chose the material which is stable in the heat transfer medium.

There may be various embodiments in the present apparatus. For example, in the embodiment shown in FIG. 1, it is a typical way of use to pack the part of the heat transfer tube 2 in the high temperature compartment 1A with a catalyst to carry out the above mentioned oxidation reaction, and to keep the rest of the tube in the low temperature compartment empty to provide a quenching zone of the reaction product fluid. In the quenching zone, the heat transfer tube may be packed with solid particles inert to the reaction. Also, it is possible to pack both parts of the high temperature side and the low temperature side of the heat transfer tube with different catalysts, and to carry out the two steps of the reaction successively at different temperatures.

The above explained ways of use are the most effective when applied to the reactor for producing (meth)acrolain and/or (meth)acrylic acid by oxidizing alpha, beta-unsaturated hydrocarbons of 3-4 carbon atoms, i.e., propylene and butenes, with a gas containing molecular oxygen.

With respect to the relation between the upper and the lower sides and the temperatures, it is preferable to assign the high temperature side to the upper part and the low temperature side to the lower part as shown in FIG. 1. In the reverse pattern, convection of the heat transfer medium easily occur in the liquid stagnation zone to decrease the insulation effect. In general, it is preferable that the depth of the stagnation zone is 5-20 mm so that the convection may not substantially occur. If it is inevitable to use the upper part as the low temperature side and the lower part as the high temperature side, it is necessary to increase the number of the insulation plates and to provide short distances therebetween, so as to cope with the above mentioned problem.

The present invention can be applied to, in addition to the above described shell-and-tube reactors, shell-and-tube type heat exchangers. The present apparatus includes those not only of the vertical type, but also of the horizontal type.

Figure 3:
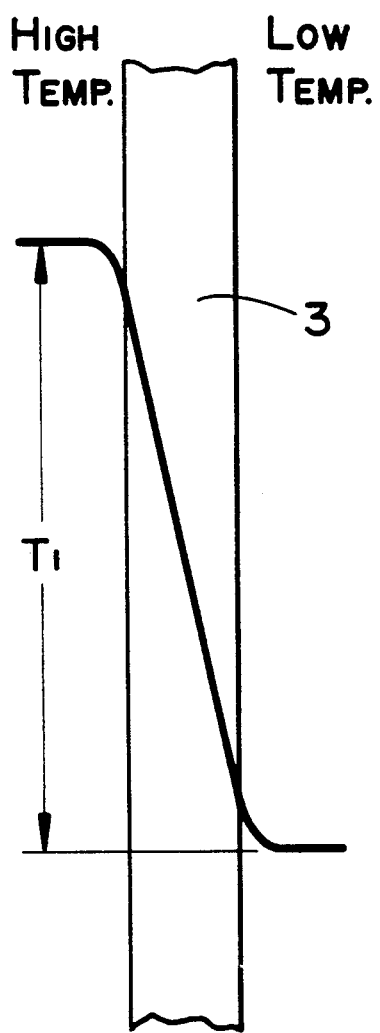
FIG. 3 and FIG. 4 are the conceptional graphs showing the temperature gradient at the intermediate tube plate to explain the effect of the present invention.
Figure 4:
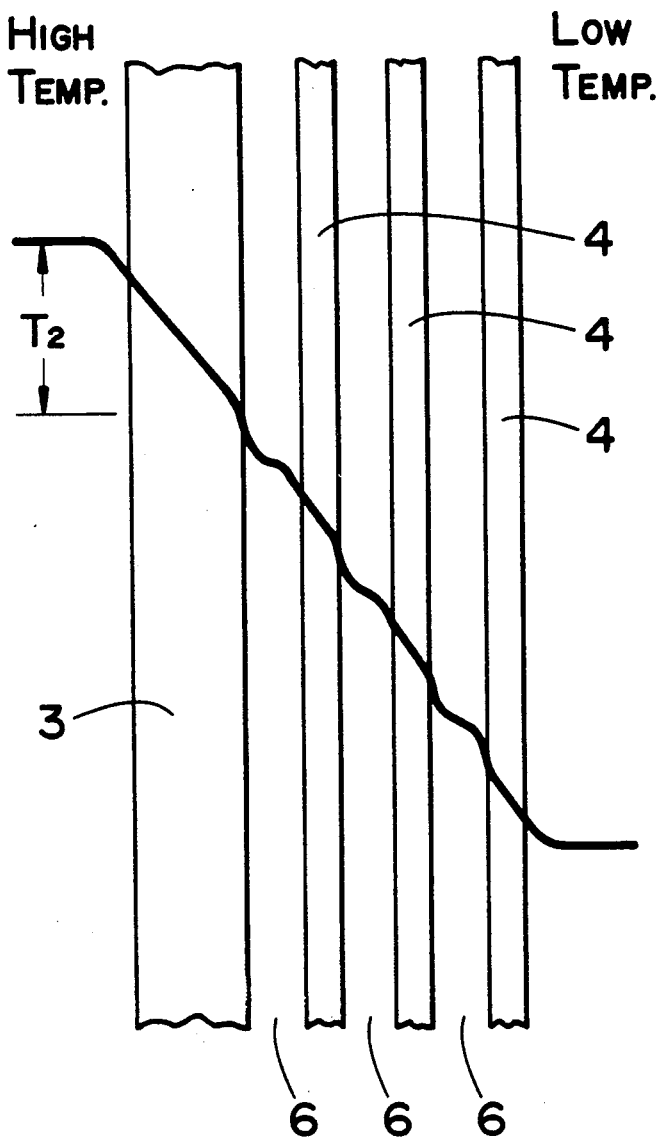

In the present shell-and-tube apparatus, use of the insulation plate or plates at one or both sides of the intermediate tube plate results in the smaller temperature difference between the high temperature side and the low temperature side of the intermediate tube plate. Now, the temperature gradient through the intermediate tube plate and the insulation plates is considered. In the conventional apparatus, as shown in FIG. 3, there is a temperature difference "$T_1$" between the both sides of the intermediate tube plate. Use of the insulation plate or plates makes the temperature difference between the both sides of the intermediate tube plate decreased to "$T_2$" as shown in FIG. 4. This suppresses the heat transfer in the intermediate tube plate, and thus, the rapid cooling effect in the quenching zone is remarkable.

Also, existence of the material of a low thermal conductivity between the two compartments suppresses heat transfer from the reaction zone of a high temperature to the quenching zone of a low temperature.

Formation of a stagnation zone between the intermediate tube plate and the insulation plate or plates, and between the insulation plates, enables that the heat transfer medium in the pool takes the role of another insulating material because it has a lower thermal conductivity, and thus, a thermal insulation effect higher than that of the simple arrangement of the insulation plates can be obtained.

Figure 6:
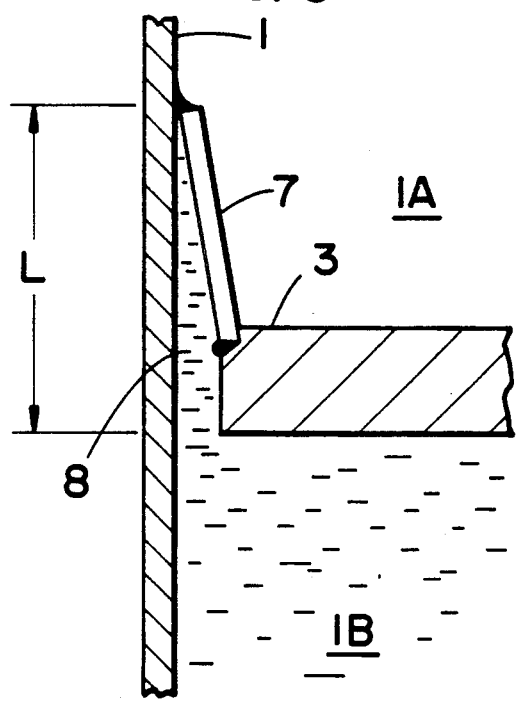
FIG. 6 and FIG. 7 are the sectional views showing various embodiments of the joint part of the body wall and the intermediate tube plate in the shell-and-tube apparatus according to the present invention.

The preferable embodiment of fitting up the intermediate tube plate in the above described shell-and-tube apparatus basically comprises, as shown in FIG. 6, in addition to the above explained formation of a stagnation zone of the heat transfer medium by the insulation plates, using a disk-shaped intermediate tube plate 3 of an outer diameter a little smaller than the inner diameter of the cylindrical body wall 11 to fix it through a fixing plate 7 of a short cylinder shape, so that the space 8 formed by the body wall 11, the fixing plate 7 and the periphery of the intermediate tube plate 3 may be filled with the heat transfer medium in the compartment. This structure makes the temperature gradient in the body wall to which the intermediate tube plate is attached gentle, suppresses the thermal stress in the body wall, and minimizes the possibility of damage or destruction.

Figure 7:
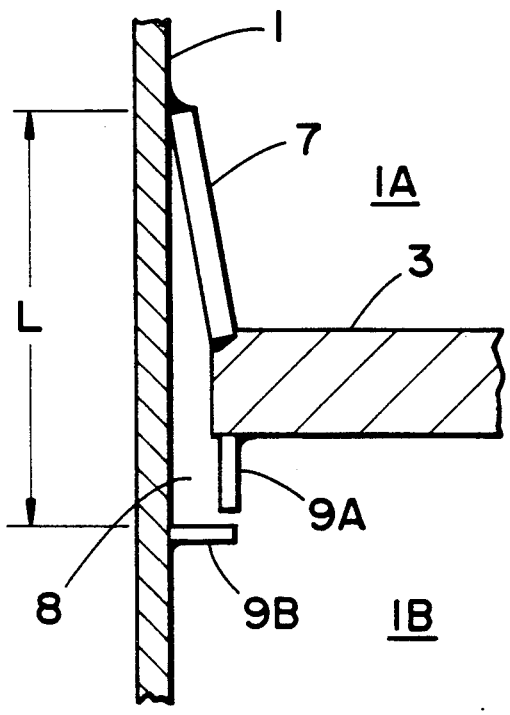

It is preferable to use, as shown in FIG. 7, a weir 9A(9B) which is fixed at one end to the intermediate tube plate or the body wall and makes a round in the body wall in the opposite side of the fixing plate of the intermediate tube plate, so as to prevent movement of the heat transfer medium. In the example shown in the drawings, there are installed two weirs extending vertically from both the intemediate tube plate and the body wall, but only one of them will do, or one weir of the L-shaped profile may be used with one end attached to either the intermediate tube plate or the body wall. Alternatively, a short tapered cylinder of the form nearly symmetrical to the fixing plate may be used with one end attached to one of the intermediate tube plate or the body wall.

The fixing plate may be installed at either the upper side or the lower side of the intermediate tube plate. As noted above, in the case where the upper compartment is at a high temperature and the lower compartment is at a low temperature, convection of the heat transfer medium occurs in the space between the intermediate tube plate and the body wall around the former, but in the contrary case where the upper compartment is at a low temperature and the lower compartment is at a high temperature, it is inevitable that the convection occurs. Therefore, a weir or weirs should be installed to prevent interchange of the heat transfer medium between the above mentioned space and the outer space.

Figure 8:
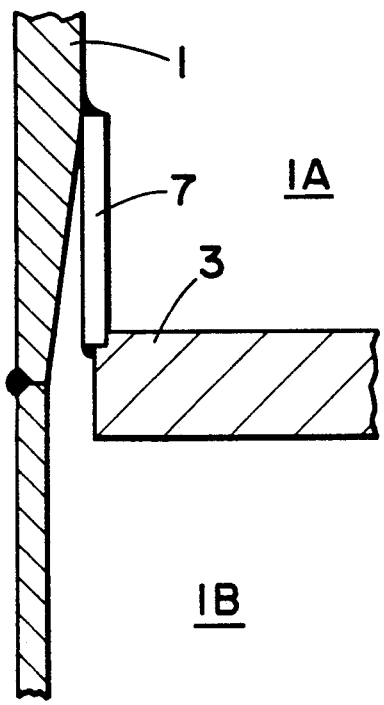
FIG. 8 is a sectional view showing another embodiment of the joint part of the body wall and the intermediate tube plate of the shell-and-tube apparatus.

The fixing plate may have the shape not only of the short tapered cylinder as shown in FIG. 6 or FIG. 7, but also of a simple cylinder as illustrated in FIG. 8, when the thickness of the body walls are significantly different in the two compartments. It is possible to manufacture the intermediate tube plate and the fixing plate in one united body.

The length of the space around the outer periphery of the intermediate tube plate 3 filled with the heat transfer medium, i.e., the vertical length "L" of the space 8 shown in FIG. 6 and FIG. 7 is to be decided in view of the temperature difference over the two compartments facing the intermediate tube plate between. In other words, the space should have the length "L" sufficient to relax the thermal stress ocurring in the body wall to which the intermediate tube plate is attached and to make the temperature gradient gentle. If the space has a longer length "L", the temperature gradient through the body wall becomes gentle, and the allowable limit of the temperature difference between the two compartments may be enlarged. The length "L" may be at longest up to 1 m, usually, up to 50 cm.

In the preferred embodiment of the present apparatus, the intermediate tube plate is attached to the body wall by the method mentioned above so as to let the heat transfer medium stay in the space where the temperature gradient of the body wall is steep in the conventional method for the purpose of making the temperature gradient gentle. This can be seen from FIG. 9 to FIG. 11; FIG. 9 shows the temperature gradient in the conventional apparatus, and FIG. 10 and FIG. 11 show the temperature gradient in the embodients of FIG. 6 and FIG. 7, respectively.

The shell-and-tube apparatus of the present invention realizes a lower energy loss due to the decreased heat transfer from the high temperature compartment to the low temperature compartment and achieves remarkable effect of quenching in the low temperature compartment. Further, because of the smaller temperature difference at both sides of the intermediate tube plate, the thermal stress ocurring in the intermediate tube plate does not become too high, and there is no risk of damaging the apparatus. The cost of manufacturing the apparatus is lower than that of the apparatus having the separately made compartments of high temperature and low temperature.

When the present invention is applied to the shell-and-tube reactor, due to the lack of the dead space between the reaction zone and the quenching zone, it is possible to immediately quench the gas after the reaction to avoid progress of the side reactions, and it is easy to carry out the two or three step reactions successively at different temperatures.

In the preferred embodiment of the present shell-and-tube apparatus, i.e., the embodiment in which the intermediate tube plate is attached to the body wall by using the fixing plate of cylindrical shape, as noted above, even if the temperature difference between the two compartments through the intermediate tube plate becomes significantly high, the thermal stress ocurring in the body wall does not become too large and there is no risk of destroying the apparatus.

The present invention will be applied to the reactors in which a high temperature reaction products are to be quenched, e.g., gas-phase oxidation of propylene or butenes, to give the advantages of reduced space of installation, improved yields and securing safety.

EXAMPLE

Figure 5A:
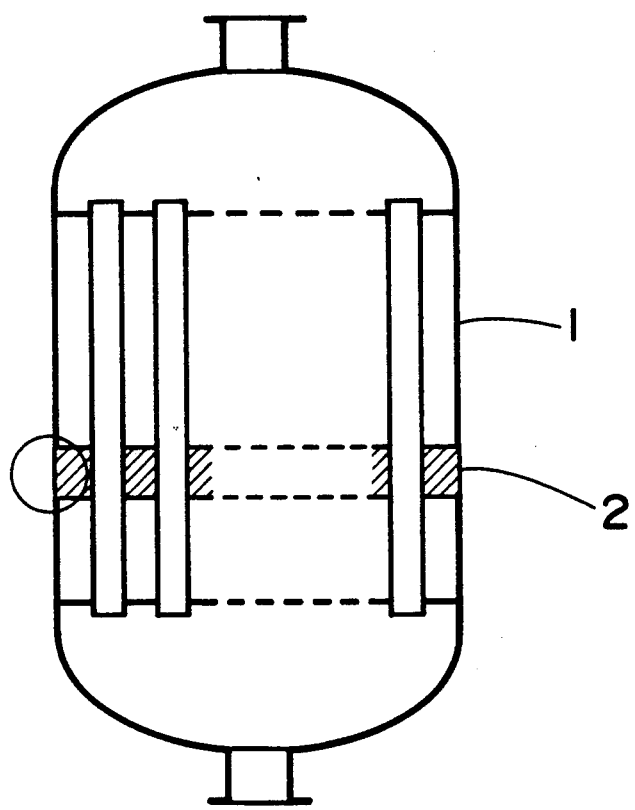
FIG. 5A and FIG. 5B are sectional views of a conventional shell-and-tube apparatus.
Figure 5B:
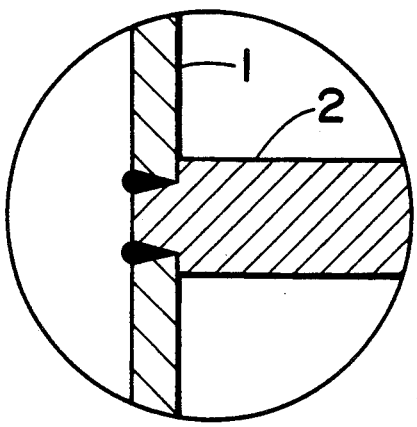

In the shell-and-tube reactor (diameter: 4 m, hight: 8 m) for gas-phase oxidation of the structure illustrated in FIG. 5, it is calculated that, in the case where a heat transfer medium of 200° C. is circulated in one compartment and the heat transfer medium of 400° C. is circulated in the other compartment, the thermal stress ocurring in the body wall will exceed the allowable limit.

On the other hand, in the reactor according to the preferred embodiment of the invention having the same dimensions and the intermediate tube plate attached to the body wall as illustrated in FIG. 6 or FIG. 7 with "L" of 20 cm, even if the temperature difference between the two compartments is as high as 200° C., the thermal stress ocurring in the body wall is calculated to be in the allowable limit.

On the basis of the above presumption, there was constructed a shell-and-tube reactor in which three insulation plates (material: carbon steel, thickness: 4.5 mm) were provided under the intermediate tube plate (material: carbon steel, thickness: 50 mm) according to the embodient illustrated in FIG. 2 and FIG. 6. The distance between the intermediate tube plate and the first insulation plate and between the insulation plates are each 15 mm. There were circulated a heat transfer medium of 400° C. in the high temperature compartment (reaction zone) and another heat transfer medium of 200° C. in the low temperatue compartment (quenching zone).

Under the steady state, the temperature difference between the both sides of the intermediate tube plate $T_2$ in FIG. 4 was 35° C.

For the purpose of comparsion, the insulation plates were removed from the above apparatus and the same measurement was made. The temperature difference through the intermediate tube plate $T_1$ reached 120°-140° C.

The ratio of the heat transfer from the high temperature compartment to the low temperature compartment in the present apparatus was about only one third of that in the conventional apparatus.

We claim:

1. A shell-and-tube apparatus which comprises a vessel, at least one intermediate tube plate sectioning the interior of the vessel into at least two compartments of different temperatures, plural heat transferring tubes fitted in apertures to penetrate the intermediate tube plate or plates, and prevent fluid transfer from one compartment to an adjacent compartment and through which a fluid passes and is heated or cooled by a heat transfer medium surrounding the tubes, at least one insulation plate provided adjacent at least one side of the intermediate tube plate; the space or spaces thus formed between said at least one insulation plate and adjacent plates providing a stagnation zone for the heat transfer medium.

2. A shell-and-tube apparatus according to claim 1, wherein the vessel has a cylindrical body wall and the intermediate tube plate is a disk having a diameter smaller than the inner diameter of the body wall, and the intermediate tube plate is attached to the body wall by means of a cylindrical fixing plate to provide a stagnation zone space for the heat transfer medium between the body wall and the fixing plate and the outer periphery of the intermediate tube plate.

3. A shell-and-tube apparatus according to claim 2, wherein a weir is provided on a side of said intermediate plate opposite said fixing plate and attached at one end to one of the intermediate plate and the body wall to prevent interchange of the heat transfer medium between the stagnation zone and said space between the body wall and the fixing plate.

4. A shell-and-tube apparatus according to one of claims 1, 2, or 3, wherein the heat transfer tubes are packed with a solid catalyst and the reaction fluid passing through the tubes is heated or cooled by the heat transfer medium surrounding the tubes so as to control the reaction.

5. A shell-and-tube reactor for producing (meth)acrolain and/or (meth)acrylic acid by oxidation of an alpha, beta-unsaturated hydrocarbon of 3-4 carbon atoms with a gas containing molecular oxygen which comprises: a vessel, at least one intermediate tube plate sectioning the interior of the vessel into at least two compartments of different temperatures, plural heat transferring tubes fitted in apertures to penetrate the intermediate tube plate or plates and prevent fluid transfer from one compartment to an adjacent compartment, and through which a fluid passes and is heated or cooled by a heat transfer medium surrounding the tubes, at least one insulation plate provided adjacent at least one side of the intermediate tube plate; the space or spaces thus formed between said at least one insulation plate and adjacent plates providing a stagnation zone for the heat transfer medium.

* * * * *